(12) United States Patent
Greenburg et al.

(10) Patent No.: US 11,234,611 B2
(45) Date of Patent: *Feb. 1, 2022

(54) INTEGRATED MULTI-FUNCTIONAL ENDOSCOPIC TOOL

(71) Applicant: Covidien LP, Mansfield, MA (US)

(72) Inventors: Benny Greenburg, Hod Hasharon (IL); Oded Zur, Kochav-Ya'ir zur Yigal (IL); Raphael Meloul, Shilo (IL)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/177,399

(22) Filed: Feb. 17, 2021

(65) Prior Publication Data

US 2021/0186361 A1 Jun. 24, 2021

Related U.S. Application Data

(60) Continuation of application No. 17/168,300, filed on Feb. 5, 2021, which is a continuation of application
(Continued)

(51) Int. Cl.
*A61B 1/012* (2006.01)
*A61B 1/018* (2006.01)
(Continued)

(52) U.S. Cl.
CPC .......... *A61B 5/06* (2013.01); *A61B 1/00096* (2013.01); *A61B 1/018* (2013.01); *A61B 1/0125* (2013.01);
(Continued)

(58) Field of Classification Search
CPC ..... A61B 1/24676; A61B 1/012; A61B 1/018; A61B 1/0125; A61B 5/065
See application file for complete search history.

(56) References Cited

U.S. PATENT DOCUMENTS 1,576,781 A 3/1926 Phillips
1,735,726 A 11/1929 Bornhardt
(Continued)

FOREIGN PATENT DOCUMENTS

CA 964149 3/1975
DE 3042343 A1 6/1982
(Continued)

OTHER PUBLICATIONS

WIPO, U.S. International Search Authority, International Search Report and Written Opinion dated Oct. 7, 2011 in International Patent Application No. PCT/US2011/040579, 8 pages.
(Continued)

*Primary Examiner* — Timothy J Neal
*Assistant Examiner* — William B Chou
(74) *Attorney, Agent, or Firm* — Carter, DeLuca & Farrell LLP

(57) ABSTRACT

A system for extending the visual capabilities and working channel of a bronchoscope including a probe having optic and/or tracking capabilities at a distal tip thereof and capable of being advanced through the working channel of a standard bronchoscope. The probe also includes a working channel through which various diagnostic and treatment tools may be advanced.

23 Claims, 14 Drawing Sheets

Related U.S. Application Data

No. 16/125,951, filed on Sep. 10, 2018, now Pat. No. 10,912,487, which is a continuation of application No. 13/474,572, filed on May 17, 2012, now Pat. No. 10,070,801, which is a division of application No. 12/501,330, filed on Jul. 10, 2009, now Pat. No. 8,932,207.

(60) Provisional application No. 61/079,678, filed on Jul. 10, 2008.

(51) Int. Cl.
    *A61B 1/267*     (2006.01)
    *A61B 1/00*     (2006.01)
    *A61B 1/12*     (2006.01)
    *A61B 5/06*     (2006.01)

(52) U.S. Cl.
CPC ............ *A61B 1/2676* (2013.01); *A61B 5/065* (2013.01); *A61B 1/00091* (2013.01); *A61B 1/126* (2013.01)

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | DeCant, Jr. et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,607,619 A | 8/1986 | Seike et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,669,172 A | 6/1987 | Petruzzi |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,679 A | 3/1989 | Shimonaka et al. |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |

(56) References Cited

U.S. PATENT DOCUMENTS

| | | |
|---|---|---|
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,951,677 A | 8/1990 | Crowley et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 4,994,069 A | 2/1991 | Ritchart et al. |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aamio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,622 A | 7/1993 | Brossoit |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,380,302 A | 1/1995 | Orth |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr et al. |
| 5,426,687 A | 6/1995 | Goodall et al. |
| 5,427,097 A | 6/1995 | Depp |
| 5,429,132 A | 7/1995 | Guy et al. |

(56) References Cited

U.S. PATENT DOCUMENTS

| | | |
|---|---|---|
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,474,075 A | 12/1995 | Goldberg et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |
| 5,503,416 A | 4/1996 | Aoki et al. |
| 5,506,102 A | 4/1996 | McDonnell |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,493 A | 11/1996 | Sauer et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,728,047 A | 3/1998 | Edoga |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,669 A | 6/1998 | Hansen et al. |
| 5,767,699 A | 6/1998 | Bosnyak et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |

(56) References Cited

U.S. PATENT DOCUMENTS

| | | |
|---|---|---|
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,865,726 A | 2/1999 | Katsurada et al. |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,876,325 A | 3/1999 | Mizuno et al. |
| 5,879,499 A | 3/1999 | Corvi |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,893,885 A | 4/1999 | Webster, Jr. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,989,185 A | 11/1999 | Miyazaki |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,068,593 A * | 5/2000 | Krauter ............... A61B 1/042 600/135 |
| 6,071,288 A | 6/2000 | Carol et al. |
| 6,073,043 A | 6/2000 | Schneider |
| 6,076,008 A | 6/2000 | Bucholz |
| 6,086,529 A | 7/2000 | Amdt |
| 6,096,050 A | 8/2000 | Audette |
| 6,104,944 A | 8/2000 | Martinelli |
| 6,112,111 A | 8/2000 | Glantz |
| 6,117,070 A | 9/2000 | Akiba |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,200,262 B1 | 3/2001 | Ouchi |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,210,378 B1 | 4/2001 | Ouchi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,246,784 B1 | 6/2001 | Summers et al. |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |
| 6,319,250 B1 | 11/2001 | Falwell et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,345,112 B1 | 2/2002 | Summers et al. |
| 6,351,659 B1 | 2/2002 | Vilsmeier |
| 6,366,799 B1 | 4/2002 | Acker et al. |
| 6,373,240 B1 | 4/2002 | Govari |
| 6,381,485 B1 | 4/2002 | Hunter et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,551,325 B2 | 4/2003 | Neubauer et al. |
| 6,580,938 B1 | 6/2003 | Acker |

(56) References Cited

U.S. PATENT DOCUMENTS

| | | |
|---|---|---|
| 6,584,174 B2 | 6/2003 | Schubert et al. |
| 6,585,639 B1 | 7/2003 | Kotmel et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,618,612 B1 | 9/2003 | Acker et al. |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,689,049 B1 | 2/2004 | Miyagi et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,711,429 B1 | 3/2004 | Gilboa et al. |
| 6,712,842 B1 | 3/2004 | Gifford, III et al. |
| 6,751,492 B2 | 6/2004 | Ben-Haim |
| 6,770,027 B2 | 8/2004 | Banik et al. |
| 6,788,967 B2 | 9/2004 | Ben-Haim et al. |
| 6,796,963 B2 | 9/2004 | Carpenter et al. |
| 6,947,788 B2 | 9/2005 | Gilboa et al. |
| 6,960,161 B2 | 11/2005 | Amling et al. |
| 6,995,729 B2 | 2/2006 | Govari et al. |
| 7,022,066 B2 | 4/2006 | Kokoi et al. |
| 7,101,380 B2 | 9/2006 | Khachin et al. |
| 7,182,756 B2 | 2/2007 | Saeed et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,668,583 B2 | 2/2010 | Fegert et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 7,892,165 B2 | 2/2011 | Nakamura |
| 7,976,458 B2 | 7/2011 | Stefanchik et al. |
| 7,998,062 B2 | 8/2011 | Gilboa |
| 8,057,385 B2 | 11/2011 | Cooper et al. |
| 8,123,722 B2 | 2/2012 | Chang et al. |
| 8,190,238 B2 | 5/2012 | Moll et al. |
| 10,912,487 B2 | 2/2021 | Greenburg et al. |
| 2001/0007918 A1 | 7/2001 | Vilsmeier et al. |
| 2001/0007925 A1 | 7/2001 | Ritchart et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2002/0026097 A1 | 2/2002 | Akiba |
| 2002/0067408 A1 | 6/2002 | Adair et al. |
| 2002/0087100 A1 | 7/2002 | Onuki et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0162555 A1 | 11/2002 | West et al. |
| 2002/0165503 A1 | 11/2002 | Morris et al. |
| 2002/0173689 A1 | 11/2002 | Kaplan |
| 2002/0193686 A1 | 12/2002 | Gilboa |
| 2003/0018251 A1 | 1/2003 | Solomon |
| 2003/0028096 A1 | 2/2003 | Niwa et al. |
| 2003/0040657 A1 | 2/2003 | Yamaya et al. |
| 2003/0074011 A1 | 4/2003 | Gilboa et al. |
| 2003/0086599 A1 | 5/2003 | Armato, III et al. |
| 2003/0114742 A1 | 6/2003 | Lewkowicz et al. |
| 2003/0142753 A1 | 7/2003 | Gunday |
| 2003/0160721 A1 | 8/2003 | Gilboa et al. |
| 2003/0171653 A1 | 9/2003 | Yokoi et al. |
| 2003/0227547 A1 | 12/2003 | Iddan |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2004/0260201 A1 | 12/2004 | Mueller |
| 2005/0033149 A1 | 2/2005 | Strommer et al. |
| 2005/0080342 A1 | 4/2005 | Gilreath et al. |
| 2005/0085715 A1 | 4/2005 | Dukesherer et al. |
| 2005/0107688 A1 | 5/2005 | Strommer |
| 2005/0119527 A1 | 6/2005 | Banik et al. |
| 2005/0197566 A1 | 9/2005 | Strommer et al. |
| 2005/0229934 A1 | 10/2005 | Willeford |
| 2005/0251005 A1 | 11/2005 | Diwan |
| 2005/0288549 A1 | 12/2005 | Mathis |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0069313 A1 | 3/2006 | Couvillon et al. |
| 2006/0149129 A1 | 7/2006 | Watts et al. |
| 2006/0149134 A1 | 7/2006 | Soper et al. |
| 2006/0184016 A1 | 8/2006 | Glossop |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0197896 A1 | 8/2007 | Moll et al. |
| 2007/0225559 A1 | 9/2007 | Clerc et al. |
| 2007/0265639 A1 | 11/2007 | Danek et al. |
| 2007/0287901 A1 | 12/2007 | Strommer et al. |
| 2007/0293721 A1 | 12/2007 | Gilboa |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0125760 A1 | 5/2008 | Gilboa |
| 2008/0132757 A1 | 6/2008 | Tgavalekos |
| 2008/0132909 A1 | 6/2008 | Jascob et al. |
| 2008/0132911 A1 | 6/2008 | Sobe |
| 2008/0139886 A1 | 6/2008 | Tatsuyama |

(56) References Cited

U.S. PATENT DOCUMENTS

| | | | |
|---|---|---|---|
| 2008/0139915 | A1 | 6/2008 | Dolan et al. |
| 2008/0144909 | A1 | 6/2008 | Wiemker et al. |
| 2008/0147000 | A1 | 6/2008 | Seibel et al. |
| 2008/0154090 | A1 | 6/2008 | Hashimshony |
| 2008/0154172 | A1 | 6/2008 | Mauch |
| 2008/0157755 | A1 | 7/2008 | Kruger et al. |
| 2008/0161682 | A1 | 7/2008 | Kendrick et al. |
| 2008/0162074 | A1 | 7/2008 | Schneider |
| 2008/0183071 | A1 | 7/2008 | Strommer et al. |
| 2008/0188749 | A1 | 8/2008 | Rasche et al. |
| 2009/0182224 | A1 | 7/2009 | Shmarak et al. |
| 2009/0234223 | A1 | 9/2009 | Onoda et al. |
| 2010/0016757 | A1 | 1/2010 | Greenburg et al. |
| 2011/0105839 | A1 | 5/2011 | Hoffman et al. |

FOREIGN PATENT DOCUMENTS

| | | | |
|---|---|---|---|
| DE | 3508730 | A1 | 9/1986 |
| DE | 3520782 | A1 | 12/1986 |
| DE | 3717871 | A1 | 12/1988 |
| DE | 3831278 | A1 | 3/1989 |
| DE | 3838011 | A1 | 7/1989 |
| DE | 4213426 | A1 | 10/1992 |
| DE | 4225112 | C1 | 12/1993 |
| DE | 4233978 | C1 | 4/1994 |
| DE | 19610984 | A1 | 9/1997 |
| DE | 19715202 | A1 | 10/1998 |
| DE | 19751761 | A1 | 10/1998 |
| DE | 19832296 | A1 | 2/1999 |
| DE | 19747427 | A1 | 5/1999 |
| DE | 10085137 | T1 | 11/2002 |
| EP | 0062941 | A1 | 10/1982 |
| EP | 0119660 | A1 | 9/1984 |
| EP | 0155857 | A2 | 9/1985 |
| EP | 0319844 | A1 | 6/1989 |
| EP | 0326768 | A2 | 8/1989 |
| EP | 0350996 | A1 | 1/1990 |
| EP | 0419729 | A1 | 4/1991 |
| EP | 0427358 | A1 | 5/1991 |
| EP | 0456103 | A2 | 11/1991 |
| EP | 0581704 | A1 | 2/1994 |
| EP | 0600610 | A2 | 6/1994 |
| EP | 0651968 | A1 | 5/1995 |
| EP | 0655138 | B1 | 5/1995 |
| EP | 0796633 | A1 | 9/1997 |
| EP | 0857461 | A2 | 8/1998 |
| EP | 0894473 | A2 | 2/1999 |
| EP | 0908146 | A2 | 4/1999 |
| EP | 0930046 | A2 | 7/1999 |
| EP | 1078644 | A1 | 2/2001 |
| EP | 1255113 | A1 | 11/2002 |
| EP | 2096523 | A1 | 9/2009 |
| FR | 2417970 | A1 | 9/1979 |
| FR | 2618211 | A1 | 1/1989 |
| GB | 2094590 | A | 9/1982 |
| GB | 2164856 | A | 4/1986 |
| JP | 63240851 | A | 10/1988 |
| JP | 03267054 | A | 11/1991 |
| JP | 06194639 | A | 7/1994 |
| JP | 07043619 | A | 2/1995 |
| JP | 10197807 | A | 7/1998 |
| JP | H11281897 | A | 10/1999 |
| JP | 2000075218 | A | 3/2000 |
| JP | 2002301018 | A | 10/2002 |
| WO | 8809151 | A1 | 12/1988 |
| WO | 8905123 | A1 | 6/1989 |
| WO | 9005494 | A1 | 5/1990 |
| WO | 9103982 | A1 | 4/1991 |
| WO | 9104711 | A1 | 4/1991 |
| WO | 9107726 | A1 | 5/1991 |
| WO | 9203090 | A1 | 3/1992 |
| WO | 9206645 | A1 | 4/1992 |
| WO | 9404938 | A1 | 3/1994 |
| WO | 9423647 | A1 | 10/1994 |
| WO | 9424933 | A1 | 11/1994 |
| WO | 9507055 | A1 | 3/1995 |
| WO | 9611624 | A2 | 4/1996 |
| WO | 9632059 | A1 | 10/1996 |
| WO | 97/29684 | A1 | 8/1997 |
| WO | 9729682 | A1 | 8/1997 |
| WO | 9736192 | A1 | 10/1997 |
| WO | 9749453 | A1 | 12/1997 |
| WO | 9808554 | A1 | 3/1998 |
| WO | 9838908 | A1 | 9/1998 |
| WO | 9915097 | A2 | 4/1999 |
| WO | 9921498 | A1 | 5/1999 |
| WO | 9923956 | A1 | 5/1999 |
| WO | 9926549 | A1 | 6/1999 |
| WO | 9927839 | A2 | 6/1999 |
| WO | 9929253 | A1 | 6/1999 |
| WO | 9933406 | A1 | 7/1999 |
| WO | 9937208 | A1 | 7/1999 |
| WO | 9938449 | A1 | 8/1999 |
| WO | 9952094 | A1 | 10/1999 |
| WO | 9960939 | A1 | 12/1999 |
| WO | 0006701 | A1 | 2/2000 |
| WO | 0010456 | A1 | 3/2000 |
| WO | 0016684 | A1 | 3/2000 |
| WO | 0035531 | A1 | 6/2000 |
| WO | 0130437 | A1 | 5/2001 |
| WO | 0167035 | A1 | 9/2001 |
| WO | 0187136 | A2 | 11/2001 |
| WO | 0187398 | A2 | 11/2001 |
| WO | 0191842 | A1 | 12/2001 |
| WO | 0224054 | A2 | 3/2002 |
| WO | 02064011 | A2 | 8/2002 |
| WO | 02070047 | A1 | 9/2002 |
| WO | 03086498 | A2 | 10/2003 |
| WO | 2004/023986 | A1 | 3/2004 |
| WO | 2005025635 | A2 | 3/2005 |
| WO | 2007109418 | A2 | 9/2007 |

OTHER PUBLICATIONS

European Patent Office, Extended European Search Report dated Sep. 6, 2011 in European Patent Application No. EP11174666.5, 6 pages.
Japanese Patent Office, Examiner's Report dated Aug. 19, 2011 in Japanese Patent Application No. JP2007-552806, 7 pages.
WIPO, U.S. International Preliminary Examining Authority, International Preliminary Reporton Patentability dated Jun. 30, 2011 in International Patent Application No. PCT/US2009/069073, 6 pages.
United States Patent and Trademark Office, Office Action dated Mar. 31, 2011 in U.S. Appl. No. 12/643,917, 10 pages.
European Patent Office, Extended European Search Report dated Mar. 8, 2011 in European Patent Application No. EP10191689.8, 4 pages.
European Patent Office, Supplementary European Search Report dated Nov. 15, 2010 in European Patent Application No. EP10159373.9, 12 pages.
United States Patent and Trademark Office, Office Action dated Oct. 4, 2010 in U.S. Appl. No. 12/271,175, 11 pages.
European Patent Office, Supplementary European Search Report dated Aug. 11, 2010 in European Patent Application No. EP03719056.8, 4 pages.
European Patent Office, Examination Report dated Mar. 30, 2010 in European Patent Application No. EP05737664.2, 5 pages.
European Patent Office, Supplementary European Search Report dated Feb. 2, 2010 in European Patent Application Mo. 04735453.5, 3 pages.
European Patent Office, Extended European Search Report dated Dec. 1, 2009 in European Patent Application No. EP09157586.0, 7 pages.
WIPO, U.S. International Search Authority, International Search Report and Written Opinion dated Nov. 12, 2009 in International Patent Application No. PCT/IL2009/000697, 9 pages.
European Patent Office, Supplementary European Search Report dated Jul. 14, 2009 in European Patent Application No. EP03719056.8, 6 pages.

(56) References Cited

OTHER PUBLICATIONS

United States Patent and Trademark Office, Office Action dated Jun. 24, 2009 in U.S. Appl. No. 10/571,695, 11 pages.
WIPO, U.S. International Search Authority, International Search Report and Written Opinion dated Mar. 16, 2009 in International Patent Application No. PCT/IB2008/002543, 9 pages.
United States Patent and Trademark Office, Final Office Action dated Mar. 12, 2009 in U.S. Appl. No. 10/597,747, 7 pages.
European Patent Office, Supplementary European Search Report dated Feb. 27, 2009 in European Patent Application No. EP03719056.8-1265, 6 pages.
European Patent Office, Supplementary European Search Report dated Oct. 7, 2008 in European Patent Application No. EP04770514.0, 4 pages.
European Patent Office, Supplementary European Search Report dated Sep. 18, 2008 in European Patent Application No. EP0477514.1, 4 pages.
United States Patent and Trademark Office, Office Action dated Sep. 11, 2008 in U.S. Appl. No. 10/597,747, 9 pages.
WIPO, U.S. International Search Authority, International Search Report and Written Opinion dated Jul. 11, 2008 in International Patent Application No. PCT-IL2005/000159, 12 pages.
WIPO, U.S. International Preliminary Examining Authority, International Preliminary Reporton Patentability dated Oct. 9, 2007 in International Patent Application No. PCT/IL2004/000843, 4 pages.
WIPO, U.S. International Search Authority, International Search Report and Written Opinion dated Sep. 24, 2007 in International Patent Application No. PCT/IL2004/000843, 4 pages.
WIPO, U.S. International Preliminary Examining Authority, International Preliminary Reporton Patentability dated Jan. 24, 2004 in International Patent Application No. PCT/IL2003/000323, 3 pages.
WIPO, U.S. International Search Authority, International Search Report dated Dec. 8, 2003 in International Patent Application No. PCT/IL2003/000323, 1 pages.
McKenna, N.J. et al., "Nuclear Receptor Coregulators: Cellular and Molecular Biology," Endocrine Reviews 20(3): 321-344, Jun. 1, 1999, 24 pages.
Ding, X.F. et al., "Nuclear Receptor-Binding Sites of Coactivators Glucocorticoid Receptor Interacting Protein 1 (GRIP1) and Steroid Receptor Coactivator 1 (SRC-1): Multiple Motifs with Different Binding Specificities," MolecularEndocrinology12:302-313, Feb. 1, 1998 (9 pages).
Stenoien, D.L. et al., "Ligand-Mediated Assembly and Real-Time Cellular Dynamics of Estrogen Receptor .alpha.-Coactivator Complexes in Living Cells," Molecular and Cellular Biology, Jul. 2001, pp. 4404-4412, 9 pages.
European Search Report for 15162795.7 dated Jul. 29, 2015.
This application is a Continuation of U.S. Appl. No. 17/168,300, filed Feb. 5, 2021, Pending.
Is a continuation of U.S. Appl. No. 16/125,951, filed Sep. 10, 2018, U.S. Pat. No. 10,912,487.
Is a continuation of U.S. Appl. No. 13/474,572, filed May 17, 2012, U.S. Pat. No. 10,070,801.
U.S. Appl. No. 12/501,330, filed Jul. 10, 2009, U.S. Pat. No. 8,932,207.

\* cited by examiner

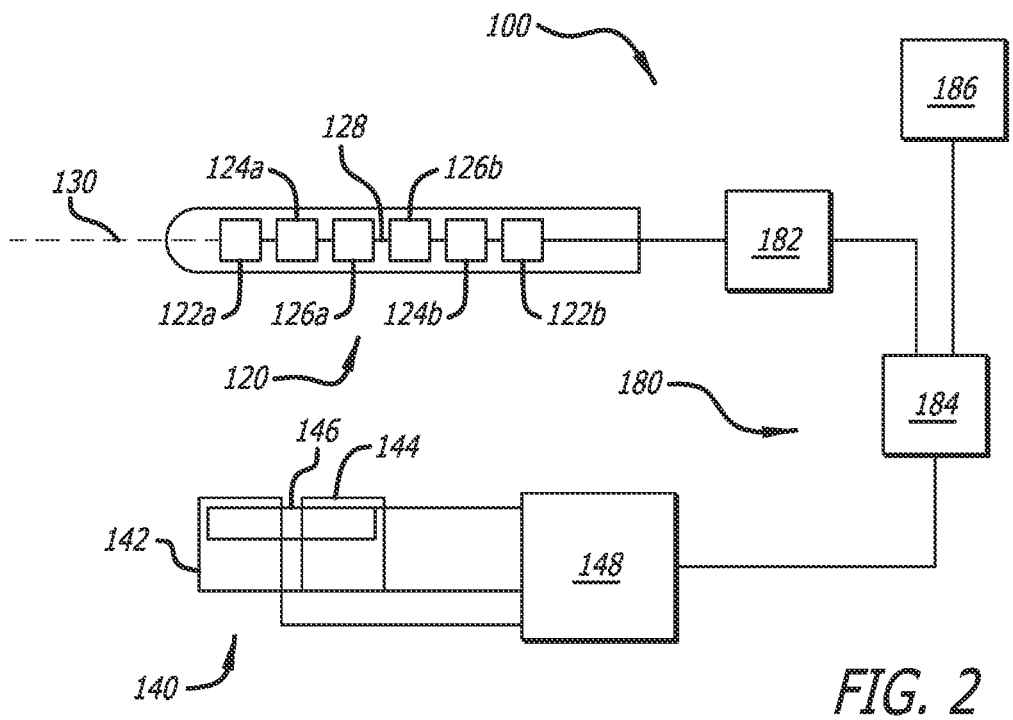
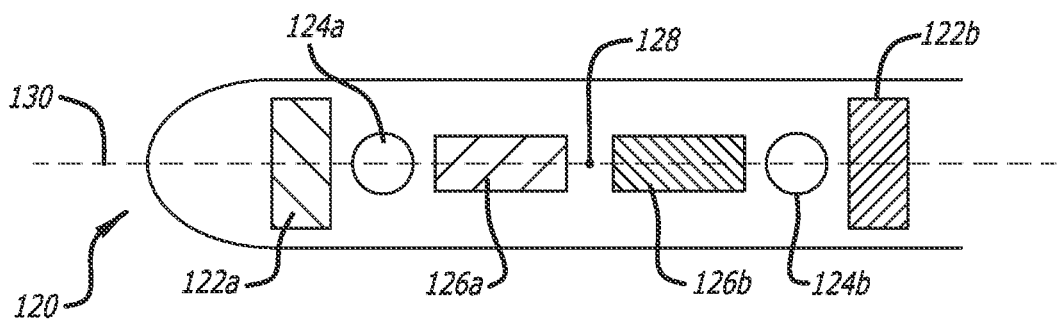
FIG. 2
FIG. 3

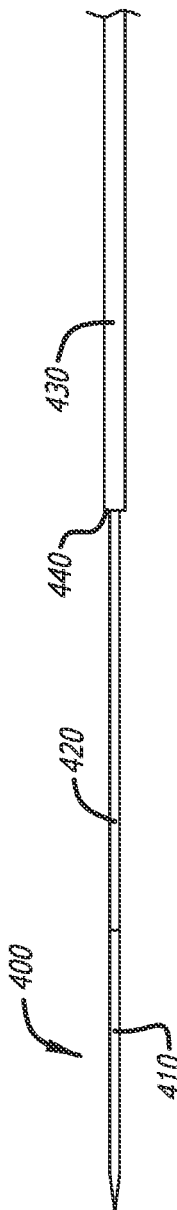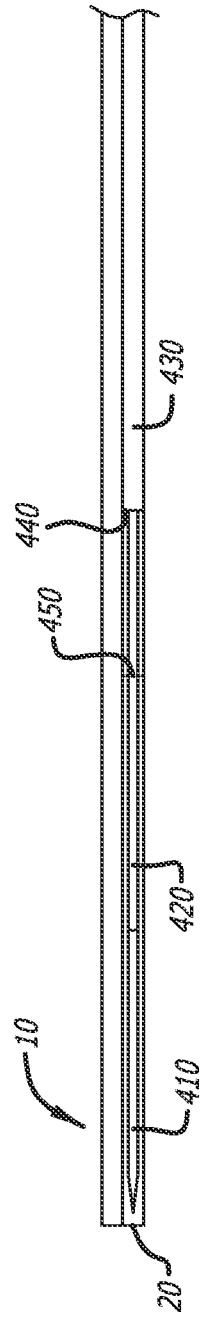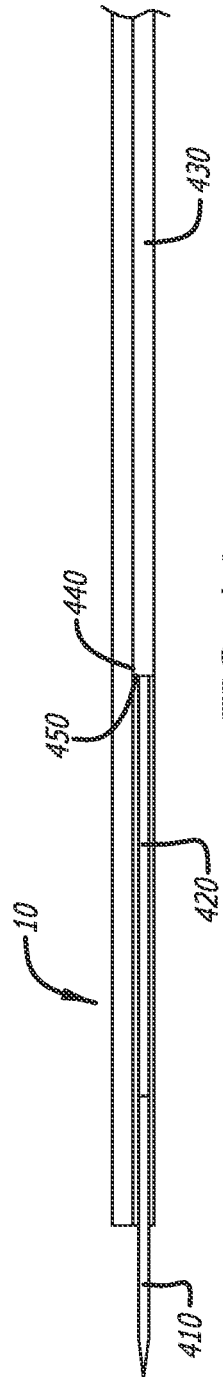

INTEGRATED MULTI-FUNCTIONAL ENDOSCOPIC TOOL

CROSS-REFERENCE TO RELATED APPLICATIONS

This application is a continuation of U.S. patent application Ser. No. 17/168,300, filed on Feb. 5, 2021, which is a continuation of U.S. patent application Ser. No. 16/125,951, filed on Sep. 10, 2018, now U.S. Pat. No. 10,912,487, which is a continuation of U.S. patent application Ser. No. 13/474,572, filed on May 17, 2012, now U.S. Pat. No. 10,070,801, which is a divisional of U.S. patent application Ser. No. 12/501,330, filed on Jul. 10, 2009, now U.S. Pat. No. 8,932,207, which claims the benefit of the filing date of provisional U.S. Patent Application No. 61/079,678, filed on Jul. 10, 2008.

BACKGROUND

Identifying and treating lung tissue abnormalities presents challenges that are somewhat unique to the lungs. If a tissue lesion or tumor is to be identified and excised surgically, the chest wall must be opened to provide access to the lungs. Opening the chest wall is a common procedure but one that presents risks of infection and lengthy recovery time, nonetheless. If a tissue lesion or tumor is to be identified endoscopically, the complicated bronchial maze must be navigated.

Bronchoscopes are small cameras attached to the end of a navigable probe and are useful in navigating the airways. The live, illuminated images provide the physician a direct look at the inside surfaces of the airways; however, these bronchoscopes have some inherent shortcomings. First, their present size limits how far into the airways they can be navigated. The airways decrease in diameter as the alveoli are approached. Second, the lungs are a moist environment and can cause the camera lens to become obscured with moisture. Similarly, if a tissue procedure, such as a biopsy, is performed in an airway that can accommodate an endoscope and a cutting tool, there is a chance that blood, mucous, or tissue may land on the lens and obscure the physician's view.

To address the first shortcoming, technology has been developed that allows a physician to track, in real-time, the position of a probe (hereinafter "locatable guide" or "LG") traveling through the airways. This technology incorporates a plurality of coils at the end of an LG and a magnetic field generator outside of the patient. The patient is placed in the magnetic field created by the generator. As the LG is navigated through the airways, electrical current is induced in the coils and sent via conductors to a computer. The computer can calculate the position and orientation of the probe based on the relative strengths of the current being induced. This technology is shown and described in greater detail in U.S. Pat. Nos. 7,233,820 6,226,543, 6,188,355, 6,380,732, 6,593,884, 6,711,429, 6,558,333, 6,887,236, 6,615,155, 6,574,498, 6,947,788, 6,996,430, 6,702,780, and 6,833,814; and U.S. Patent Publications 20050171508, 20030074011, 20020193686, each of which is incorporated by reference herein in its entirety and also PCT application WO 03/086498 titled 'Endoscope Structure and Techniques for Navigation in Brunched Structure' to Gilboa, fully incorporated herein by reference.

These references describe a method and apparatus in which a thin locatable guide, enveloped by a sheath, is used to navigate a bronchoscopic tool to a target location within the lung, aimed in particular to deliver treatments to the lung periphery beyond the bronchoscope's own reach. The coordinates of the target are predetermined based upon three-dimensional CT data. A location sensor is incorporated at the locatable guide's tip. The enveloped guide is inserted into the lung via the working channel of a bronchoscope. First, the bronchoscope's tip is directed to the furthest reachable location in the direction of the target. Next, the guide is advanced beyond the tip of the bronchoscope towards the designated target, based on the combination of the CT data and the position of the guide's tip as measured in body coordinates. When the guide's tip is at the target, the guide is withdrawn, freeing the sheath for insertion of a bronchoscopic tool. In order to prevent the distal end portion of the sheath from sliding away from the target, the sheath is locked to the bronchoscope's body and the bronchoscope itself is held steadily to prevent it from slipping further into the lungs or outwards. Because the airways in the periphery of the lung are narrow, approximately in the same dimensions as the sheath, sideways movements are extremely limited.

The above system and apparatus are aimed to navigate standard bronchoscopic tools to a target located in the lung. In its basic operation, first the target is identified in the CT data, then the guide is navigated to the target and a medical treatment is delivered. It would be advantageous, however, to perform more sophisticated treatments, such as by combining different types of treatments into a single session. Because these locatable guides are smaller than endoscopes, they can travel deeper into the airways. Additionally, rather than relying on visible landmarks and the physician's knowledge of the anatomy of the airways, the position of the LG is superimposed on a computer rendering or x-ray image of the lungs, thereby increasing the navigation value of the sensor. Advantage may be taken of both technologies by placing a probe within a working channel of the endoscope. Thus, real-time images may be viewed while navigating the endoscope as far into the airways as its size allows. Then, the LG is advanced out of the distal end of the working channel of the bronchoscope and deeper into the airways. The LG is surrounded by a sheath. In some embodiments the sheath is steerable and in others, the LG itself is steerable.

Once the LG has been navigated to a target area, presently the LG is retracted through the sheath, while the sheath is left in place. The sheath is referred to as an "extended working channel" ("EWC") because it is effectively an extension of the working channel of the bronchoscope. The EWC is then used as an avenue for inserting working tools to the target site. Such tools include biopsy needles, ablation devices, etc. After the LG is removed from the EWC, the physician is operating blind, relying on the EWC to remain fixed at the target site. If a tool, such as an aspiration needle or an ablation tool, is being used that requires repositioning in order to treat a greater target area, the repositioning must be done without guidance.

There is a need for an apparatus that allows a physician to operate on a target site endoscopically, while benefiting from the concurrent use of a bronchoscope, an LG, or both. There is a further need for an endoscopic tool that has the capability of maintaining a clear lens during a procedure in a moist environment.

SUMMARY

The present disclosure represents a step forward in endoscopic procedures by providing an endoscopic tool that is capable of being inserted into narrow passageways and performing procedures once a target has been reached. Preferably the instrument of the present disclosure is insertable through the working channel of a standard bronchoscope.

More specifically, the present disclosure is a catheter designed to be extended out of the distal end of the working channel of a bronchoscope. The catheter includes a micro-camera with a means for cleaning the lens thereof in situ. Additionally, the catheter includes a location sensor capable of either transmitting a location signal or detecting location fields such that location and orientation data may be provided to the practitioner.

Additionally, the catheter of the present disclosure includes one or more miniature working channels capable of receiving diagnostic and therapeutic tools and catheters, such as biopsy or ablation tools and catheters. Other examples of diagnostic and therapeutic tools for use with the device of the present disclosure include various needles, forceps, guide catheters, cyrocatheters, needle aspiration catheters, modified athereoctomy devices, just to name a few. The combination of the camera, the miniature working channel, and the sensor, provides the practitioner with a real-time view of the tissue being manipulated during the procedure. The practitioner also has an unprecedented degree of confidence that the tissue being manipulated is the targeted tissue.

One aspect of the present disclosure uses the devices of the present disclosure for applications such as integrated in situ diagnostic techniques (AF, ULS, OCT, etc.), delivering pre-therapy tools to direct subsequent therapeutic procedures such as markers to guide radiosurgery or inject dye to direct VATS procedures, therapeutic delivery such as LDR brachy seeds or site-specific drug delivery.

BRIEF DESCRIPTION OF THE DRAWINGS

FIG. 2 is a diagram of the basic components of an embodiment of the location system of the present disclosure;

FIG. 3 is an elevation of an embodiment of a sensor assembly of the present disclosure;

FIG. 12 is a plan view of an embodiment of a tool of the present disclosure;

FIG. 13 is a plan view of an embodiment of a tool of the present disclosure within an embodiment of a catheter of the present disclosure;

FIG. 14 is a plan view of an embodiment of a tool of the present disclosure within an embodiment of a catheter of the present disclosure;

DETAILED DESCRIPTION

Figure 1:
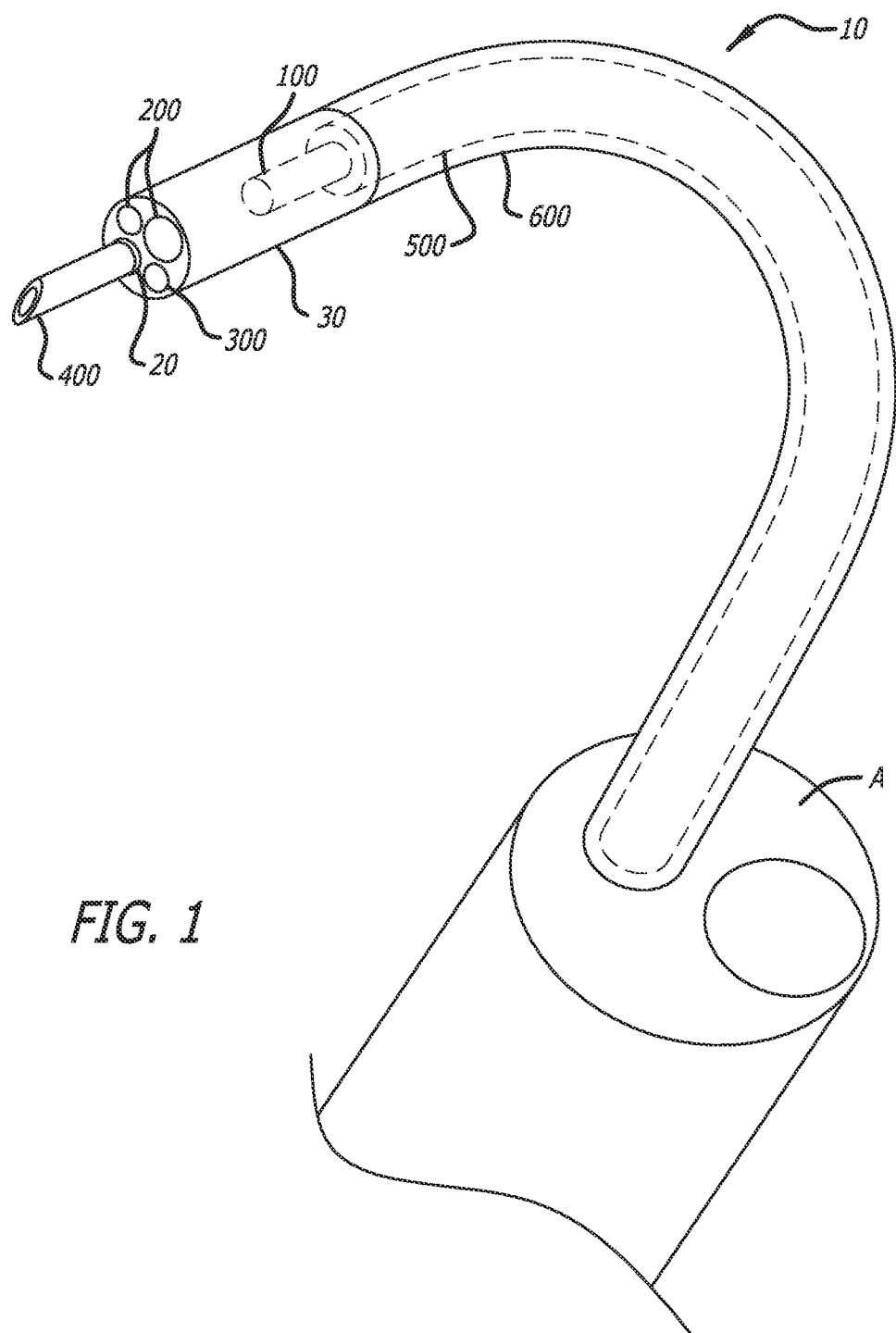
FIG. 1 is a perspective view of a general embodiment of the device of the present disclosure.

Referring now to FIG. 1, there is shown a general embodiment of the catheter 10 of the present disclosure. The embodiment in FIG. 1 is described as "general" because it is being used as a platform to introduce the various aspects and components of the present disclosure, which will then be discussed separately in more detail. Hence, FIG. 1 shows that the catheter 10 is sized to extend from the distal end of a working channel of a standard bronchoscope A. For example, some common bronchoscopes have working channels with an internal diameter of about 2.8 mm, while others have working channels with an internal diameter of about 2.65 mm. Hence, the catheter 10 has an outside diameter of 2.8 mm, or slightly less, or preferably 2.65 mm, or slightly less, such that is slides freely within the working channels of these bronchoscopes A. The catheter 10 generally includes a working channel 20, a location system 100 (only a component of which is shown in FIG. 1), an optical system 200, an optic cleaning system 300, a tool 400, a steering mechanism 500, and a catheter body 600. It is to be understood that the catheter 10 of the present disclosure is considered to be any device containing one or more of these features, in any of their respective variations discussed below, in any combination. These components are being described individually specifically so as not to limit the scope of the present disclosure to one or more combinations of these features. One skilled in the art will quickly realize that the number of components of the catheter 10, each described in various forms below, would result in too many combinations to practically describe individually.

Location System 100

The location system 100, shown in FIGS. 2-X, generally includes a sensor assembly 120, a location board 140, and a control system 180.

The sensor assembly 120 may be passive or active. A system using a passive sensor assembly 120 is shown in FIGS. 2-6 and also in U.S. patent application Ser. No. 12/417,381 filed Apr. 2, 2009 entitled Magnetic Interference Detection System and Method, which claims priority to provisional application Ser. Nos. 61/042,191, filed Apr. 3, 2008, and 61/042,578, filed Apr. 4, 2008 entitled Magnetic Interference Detection System and Method, all of which are incorporated by reference herein in their entireties. The sensor assembly 120 of the passive system is a receiver that generally includes a plurality of (preferably three) field component sensors 122, 124 and 126. Each of the field sensor components is arranged for sensing a different component of an electromagnetic field generated by the location board 140. Alternatively, the field sensor components could use ultrasound technology, or a combination of electromagnetic and ultrasound technologies.

In one embodiment, shown in FIGS. 2 and 3, each field component sensor 122, 124 and 126 includes two sensor elements, 122a, 122b, 124a, 124b, 126a, and 126b, respectively. Typically, the sensor elements are coils of wire, and the sensed components are independent magnetic field components. The coils may be formed by wrapping wire around a core. The core may then be removed to form an air core at the center of the coil or may be left in place, forming a solid core coil. Preferably, the solid core coils are made of a material such as ferrite or another material having similar magnetic properties.

Preferably, the sensor elements 122, 124 and 126 are arranged in the locatable guide 120 such that the sensor elements 122a and 122b are on opposite sides of, and equidistant from, a common reference point 128. Similarly, sensor elements 124a and 124b are on opposite sides of, and equidistant from, point 128, and sensor elements 126a and 126b also are on opposite sides of, and equidistant from, point 128. In the illustrated example, the sensors 122, 124 and 126 are disposed collinearly along a longitudinal axis 130 of the sensor assembly 120, but other configurations are possible.

Figure 4A:
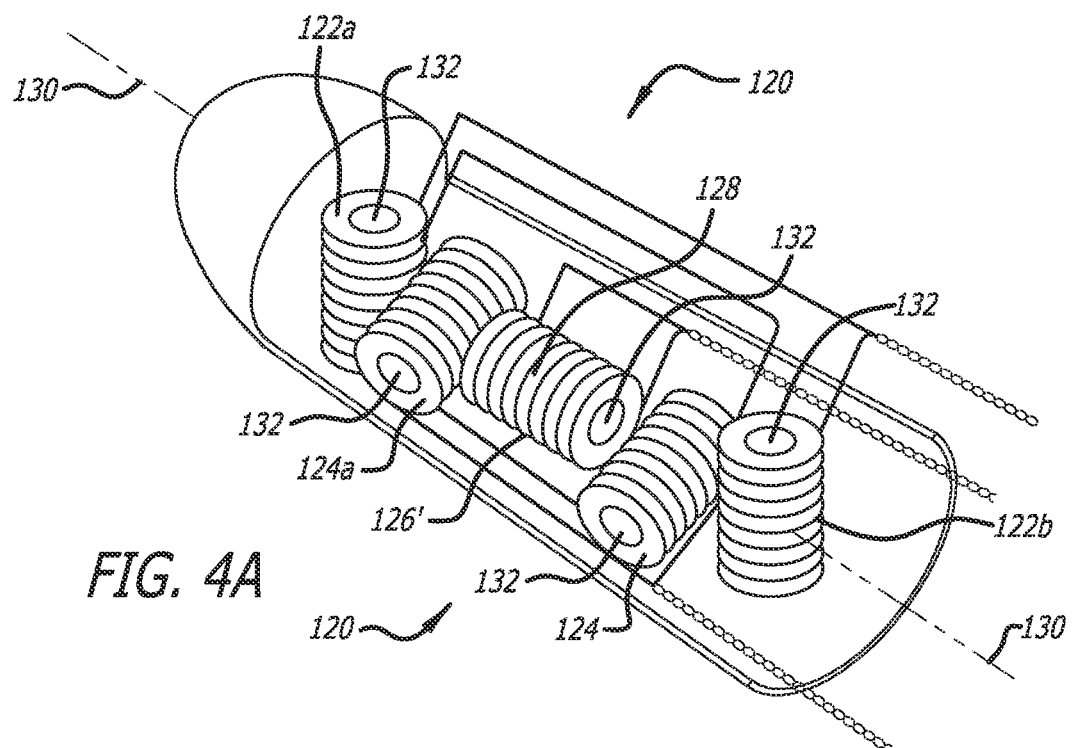
FIG. 4A is a perspective view of an embodiment of a sensor assembly of the present disclosure.
Figure 4B:
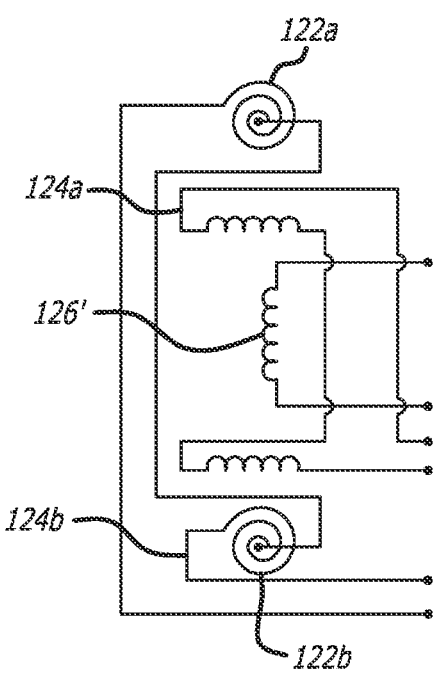
FIG. 4B is a circuit diagram of the sensor assembly of FIG. 4A.

For example, FIG. 4 shows a sensor assembly 120 having field sensor components 122, 124 and 126'. Field sensor components 122 and 124 each have two sensor elements 122a and 122b, and 124a and 124b, respectively. Sensor elements 122a and 122b are on opposite sides of, and equidistant from, point 128. Sensor elements 124a and 124b are on opposite sides of, and equidistant from, point 128. However, field sensor component 126' consists of a single coil centered on point 128.

Figure 5:
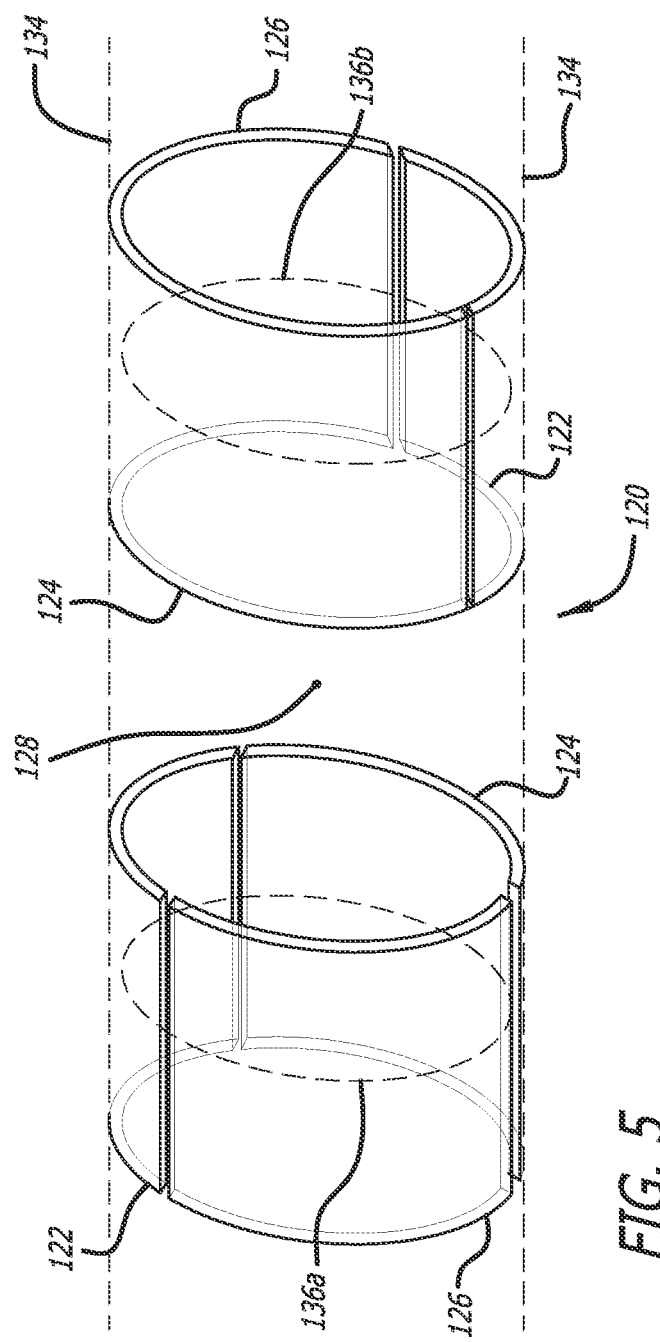
FIG. 5 is a perspective view of an embodiment of a sensor assembly of the present disclosure.

FIG. 5 shows an embodiment wherein the field sensor components 122, 124 and 126 each include two sensor elements 122c and 122d, 124c and 124d, and 126c and 126d, respectively. Each sensor element is a flat rectangular coil, of many turns of conducting wire that is bent into an arcuate shape to conform to the shape of the cylindrical surface. The dashed lines 134 and dashed circles 136 in FIG. 5 denote a conceptual cylindrical surface. The sensor elements 122c, 124c and 126c are interleaved around circle 136a. The sensor elements 122d, 124d, and 126d are interleaved around circle 136b. The sensor elements 122c and 122d are preferably disposed symmetrically with respect to the reference point 128, meaning that sensor elements 122c and 122d are on opposite side of reference point 128, are equidistant from reference point 128 and are oriented so that an appropriate 180-degree rotation about point 128 maps sensor 122c into sensor 122d. Similarly, sensor elements 124c and 124d are disposed symmetrically with respect to reference point 128, and sensor elements 126c and 126d are disposed symmetrically with respect to reference point 128.

Figure 6:
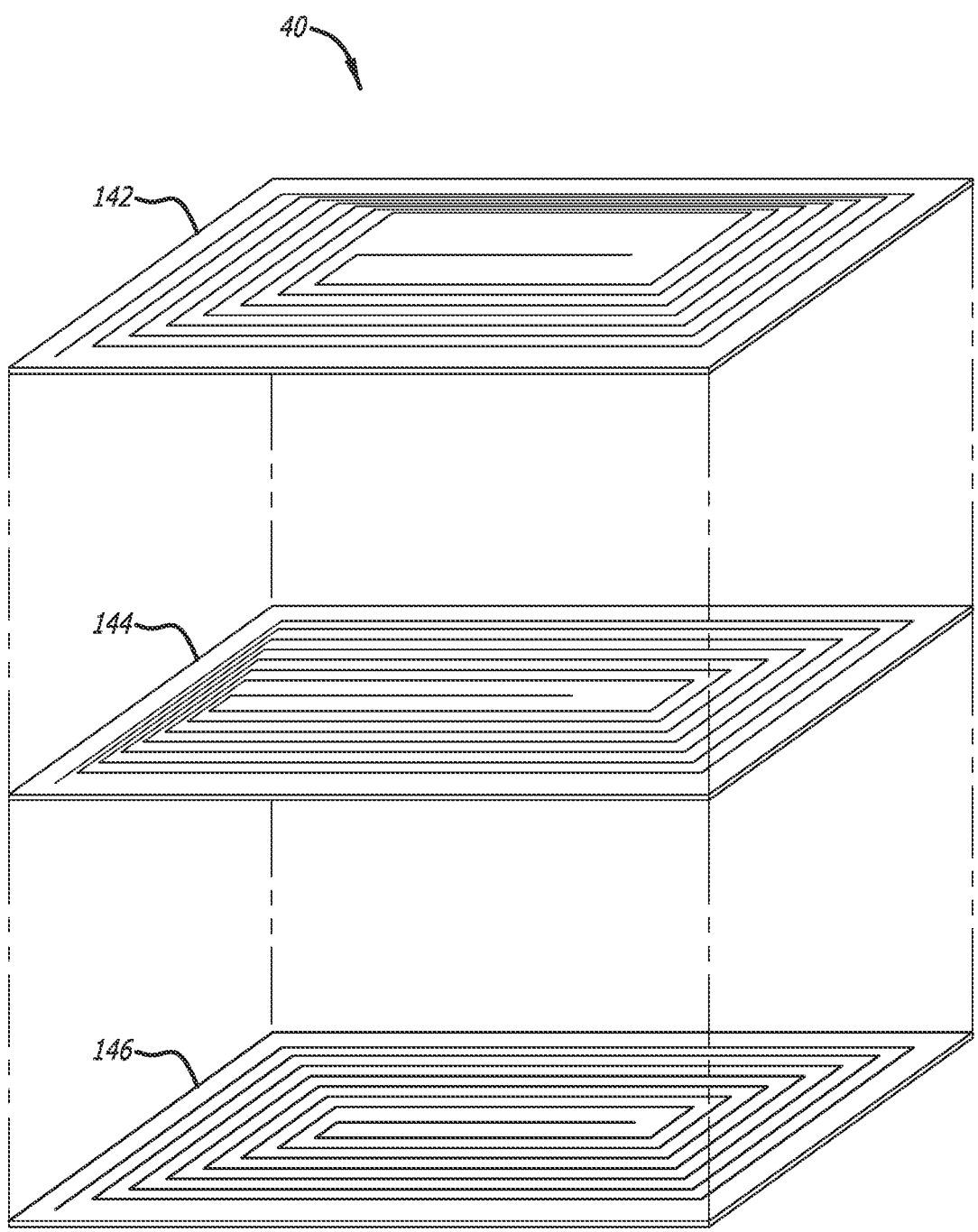
FIG. 6 is an exploded view of an embodiment of a location board of the present disclosure.

Referring again to FIG. 2, the location system 100 also includes the location board 140. The location board 140 is a transmitter of electromagnetic radiation. The location board 140 includes a stack of three substantially planar rectangular loop antennas 142, 144 and 146 connected to drive circuitry 148. FIG. 6 provides an expanded view of the loop antennas 142, 144 and 146 of the location board 140 in an expanded view to show the details of their configurations.

Antenna 142 is skewed in a y direction in that the loops on one side of the antenna 142 are closer together than the loops on the opposite side. Hence, antenna 142 creates a magnetic field that is stronger on the side where the loops are close together than it is on the opposite side. By measuring the strength of the current induced by the antenna 142 in the sensor assembly 120, it can be determined where the sensor assembly 120 is located in a y direction over the antenna 142.

Antenna 144 is similarly skewed but in an x direction. Hence, the antenna 144 also creates a magnetic field that is stronger on the side where the loops are closer together than it is on the opposite side. By measuring the strength of the current induced by the antenna 144 in the sensor assembly 120, it can be determined where the sensor assembly 120 is located in an x direction over the antenna 144.

Antenna 146 is not skewed. Rather, it creates a uniform field that naturally diminishes in strength in a vertical direction when the location board is horizontal. By measuring the strength of the field induced in the sensor assembly 120, it can be determined how far the locatable guide is located above the antenna 146.

In order to distinguish one magnetic field from another, the fields of each antenna 142, 144 and 146 are generated using independent frequencies. For example, antenna 142 might be supplied with alternating current oscillating at 2.5 kHz, antenna 144 might be supplied with alternating current oscillating at 3.0 kHz, and antenna 146 might be supplied with alternating current oscillating at 3.5 kHz. Hence, each of the field sensors 122, 124, and 126 of the locatable guide will have three different alternating current signals induced in its coils.

Driving circuitry 148 includes appropriate signal generators and amplifiers for driving each of the loop antennas 142, 144 and 146 at their corresponding frequencies. The electromagnetic waves generated by the location board 140 are received by the sensor assembly 120 and converted into electrical signals that are then sent to the control system 180, shown diagrammatically in FIG. 2.

The control system 180 generally includes reception circuitry 182 that has appropriate amplifiers and A/D converters. The reception circuitry 182 and the driving circuitry 148, which may be considered part of the control system 180, are controlled by a controller/processor 184 that typically is an appropriately programmed computer. The controller/processor 184 directs the generation of transmitted signals by driving circuitry 148.

A location system 100 using an active sensor assembly 120 is shown and described in U.S. Pat. No. 6,188,355 to Gilboa, entitled Wireless Six-Degree-of-Freedom Locator. The entirety of the patent is incorporated by reference herein. The principles of operation are similar to the operation of the passive sensor assembly system except that electrical current is sent to the sensor assembly 120, such that magnetic fields are generated thereby. These magnetic fields are then detected by other sensors and that information is used to determine a location of the probe in which the sensor assembly 120 is located.

Optic System 200

Figure 7:
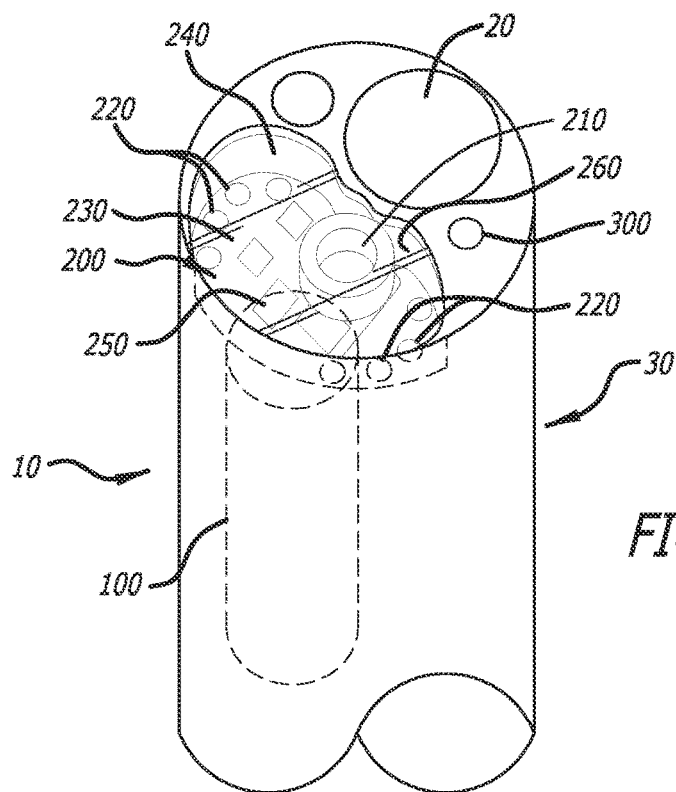
FIG. 7 is a perspective view of an embodiment of an optic system of the present disclosure.
Figure 8:
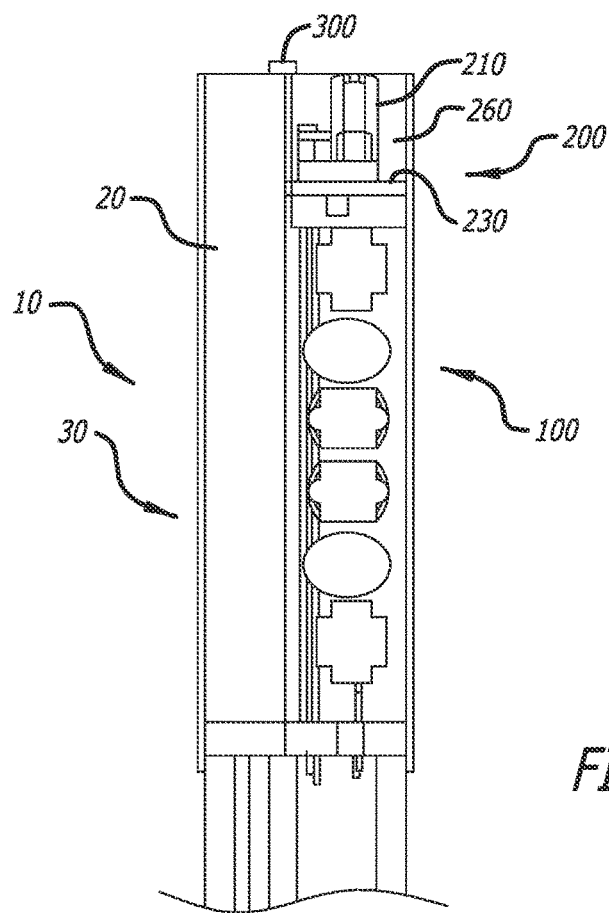
FIG. 8 is an elevational cutaway view of a distal tip of an embodiment of the catheter of the present disclosure.

Referring to FIGS. 7 and 8, the optic system 200 generally includes an objective lens 210 and one or more light sources 220, all preferably contained under a sealed optic window 240. The optic system 200 may operate within or outside of the visible spectrum. As an example only, the optic system 200 may be an infrared system. If an optic cleaning system 300, described below, is to be used, it may be preferably to make the optic window 240 flush with the distal end of the catheter 10, thereby increasing the effectiveness of the cleaning system 300.

If, however, a wide-angle view is desired, there may be utility in providing a convex optic window 240 that protrudes from the distal tip 30 of the catheter 10. This may allow the lens 210 to be closer to, or beyond the distal tip 30 of the catheter body.

The objective lens 210 may be borrowed from existing technology such as a CMOS, fiberscope or a microvideo system. The lens 210 may also be a hybrid between fiberscope and video technology, such as that found on the Olympus BF type XP160F, also marketed as the Evis Exera Bronchofibervideoscope (hereinafter "Olympus scope").

The Olympus scope includes a 1.2 mm working channel for a tool but, unlike the present disclosure, does not have an optical cleaning system, does not have a location system, and does not fit within a 2.65 mm working channel. The Olympus scope has an outside diameter of 2.8 mm.

Nevertheless, the lens system of the Olympus scope may have application in the catheter of the present disclosure. The Olympus scope uses a single, relatively large, light source. The present disclosure provides a plurality of individual, very small fibers, each acting as light guides 220 to illuminate the target. By providing a plurality of small light sources 220, rather than one larger light source, more space-saving options become available and it is possible to reduce the overall diameter of the catheter 10.

The light fibers 220 terminate at a floor 230 of the optic system 200. A space between the floor 230 and the optic window 240 provides room for additional components 250 and also results in an internal sidewall 260 surrounding the floor 230. In one embodiment, this sidewall includes a reflective material, which acts to maximize the amount of light being transmitted through the optic window 240.

As best seen in FIG. 8, the optic system 200 has a relatively short axial length. This leaves room immediately below (proximal) the optic system 200 for the sensor assembly 100. The light fibers 220 have room around the outside of the sensor assembly 100 to travel the length of the catheter for connection to a light source (not shown).

Optic Cleaning System 300

Figure 9:
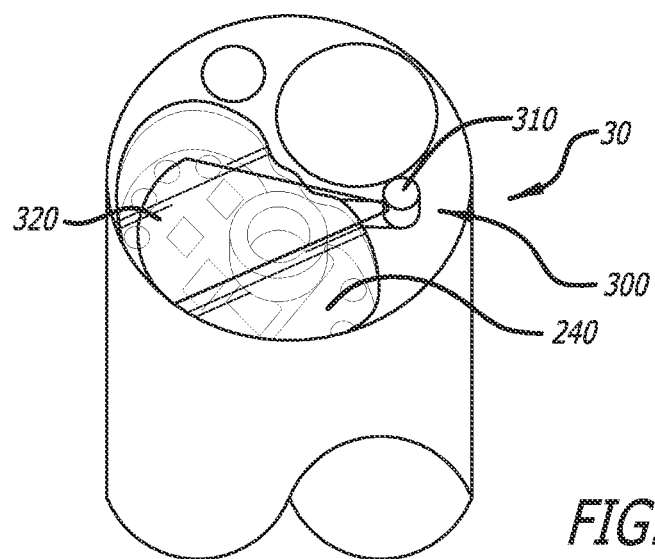
FIG. 9 is a perspective view of an embodiment of an optical cleaning system of the present disclosure.
Figure 10:
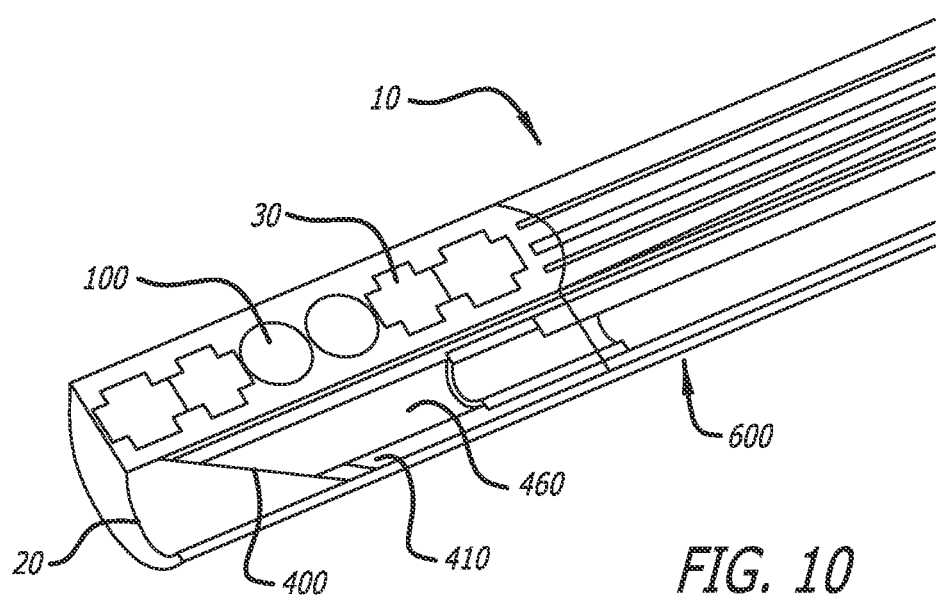
FIG. 10 is a perspective cutaway view of a distal tip of an embodiment of the catheter of the present disclosure.

The optic cleaning system 300 is shown generally in FIG. 9. The optic cleaning system 300 includes a nozzle 310 located at the distal tip 30 of the catheter 10 and directed toward the optic window 240. The nozzle 310 is supplied via a lumen with a pressurized liquid or gas. The nozzle directs a stream 320 of the pressurized liquid or gas onto the optic window 240 in order to mechanically remove and/or chemically clean mucous, blood, tissue or other debris from the optic window 240. The liquid or gas may be any liquid or gas that can be absorbed by the lungs or exhaled without harming the patient. Liquids may include water, saline, and the like. Gases may include oxygen, nitrogen, helium, air, and the like.

Preferably, the optic cleaning system 300 is fed by a small supply of liquid or gas that is located in a portion of the catheter system 10 that remains outside of the patient, such as the handle. Similarly, locating the valve associated with the actuating system near the supply, as opposed to near the nozzle 310, will reduce the amount of space occupied by the cleaning system 300. If, on the other hand, space along the length of the catheter 10 is in short supply, but there is room for a small reservoir at the tip 30 of the catheter, it is envisioned that a reservoir and valve mechanism be located at the tip 30 and electrically controlled by a small wire running the length of the catheter 10, obviating the need for a supply lumen.

Tool 400

The catheter 10 includes a working channel 20, preferably having an outside diameter of about 1.2 mm, that can accommodate a tool 400. The tool 400 may be any endoscopic tool, such as forceps, graspers, brushes, markers, seeds, ablation tools, and the like. By way of example only, several embodiments of a tool 400 are discussed in greater detail herein.

Referring now to FIGS. 10-14, there is shown a needle embodiment of the tool 400. This tool 400 includes a needle tip 410 attached to the distal end of a flexible tube 420. The flexible tube 420 may then be attached to the distal end of a larger flexible tube 430. This arrangement creates a shoulder 440 between the tubes 420 and 430, which can be used as a stop that limits the extent to which the needle tip 410 may be extended from the distal end of the catheter 10.

The example shown in FIG. 12 includes a needle tip 410, which is a 20 gauge needle having an outside diameter of approximately 0.9 mm. The length of the needle tip 410 is approximately 19 mm. It is understood that the length of the needle tip 410 should be selected considering the task the needle tip 410 is to be given as well as the target location. Because the needle is generally inflexible, a longer needle tip 410 will result in a longer inflexible tip portion 30 of the catheter 10, which in turn hampers the navigability of the catheter 10.

The flexible tube 420 may be made of any suitable, biocompatible material having a desired amount of flexibility and axial strength. A material selected for the embodiment of FIG. 12 is transparent nylon. The outside diameter of flexible tube 420 preferably matches the outside diameter of the needle tip 410. The length of the flexible tube 420 is selected to place the shoulder 440 in a desired position to interact with a stop 450 (FIGS. 13 and 14) and result in a desired maximum extension length of the needle tip 410. It is envisioned that the flexible tube 420 may have a friction fit with the larger flexible tube 430 such that the effective length of the flexible tube 420 may be adjusted for a given procedure by sliding the flexible tube 430 into or out of the larger flexible tube 430 prior to the procedure.

The larger flexible tube 430 of this embodiment is a PEEK tube with an outside diameter of 1.15 mm and extends to the handle of the bronchoscope. The difference in outside diameter of the flexible tube 420 (in this example, 0.9 mm) and the outside diameter of the larger tube 430 (in this example, 1.15 mm) results in the shoulder 440. Hence, in this example, the shoulder 440 has a height of 0.125 mm.

FIGS. 13 and 14 show the tool 400 in retracted and extended positions, respectively. In the retracted position of FIG. 13, the needle tip 410 is completely contained within the working channel 20 of the catheter 10. A separation exists between the shoulder 430 and a needle stop 450 within the working channel 20.

In the extended position of FIG. 14, the needle tip 410 protrudes beyond the distal tip 30 of the catheter 10. The shoulder 440 abuts against the stop 450, thereby preventing the needle 410 from being extended further.

Figure 11:
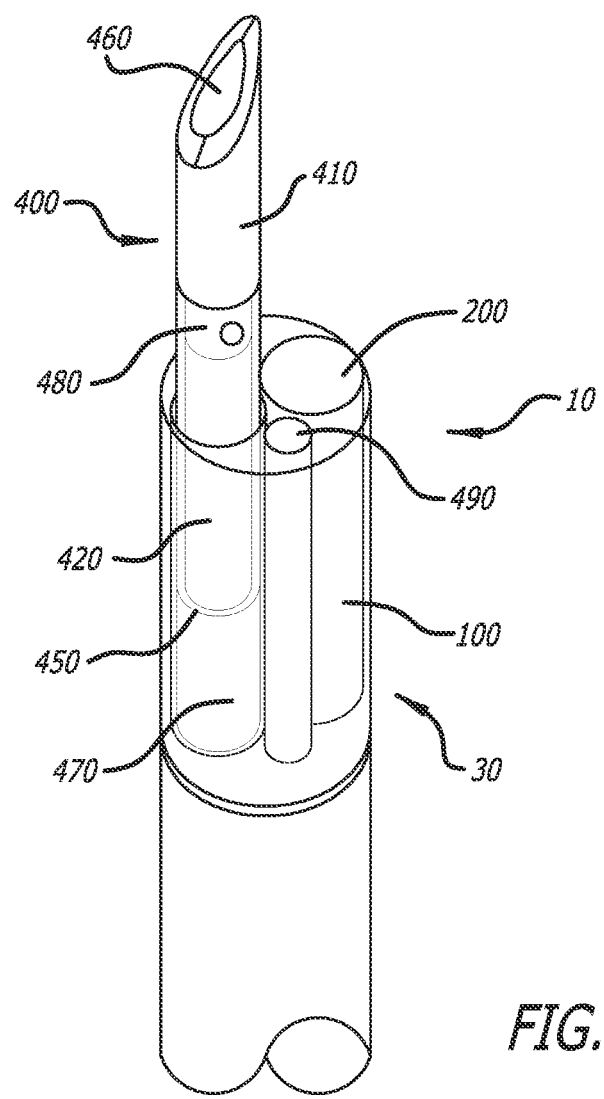
FIG. 11 is a perspective view of a distal tip of an embodiment of the catheter of the present disclosure.

Needle uses are known in the art and are applicable to the needle 410 of the present disclosure. For example, the needle tip 410, the flexible tube 420 and the larger flexible tube 430 all have a central lumen which can be made to create one continuous lumen 460 throughout the tool 400. This lumen 460 can be used to apply suction to the tool 400, thereby creating an aspirating needle or a biopsy needle. The lumen 460 can also be used as an irrigation port or a means for injecting substances into the target. Alternatively, as shown in FIG. 11, a separate irrigation lumen 490 can be provided in catheter 10 to be used in conjunction with aspirating suction applied to the tool 400.

If the needle 410 is to be used for biopsy purposes, one skilled in the art will realize that it may be desirable to keep the tissue sample contained within a distal section of the needle 410 for easy retrieval of the sample after the procedure. In this case the needle lumen 460 may be larger than a suction lumen 470, as seen in FIG. 11. Hence, a stop 480 is created that prevents the tissue from traveling too far into the catheter 10.

One embodiment of the present disclosure uses a needle tip 410 or other suitable delivery device to inject one or more markers into the target site. Markers, such as gold markers, can be used as fiducials in an image-guided radiosurgery treatment during interstitial radiation. The insertion of internal fiducial markers into various organs assists in precise setup and real-time tumor tracking during radiotherapy. Markers may also be used to adjust the center of mass of the target volume to a planned position for an upcoming treatment. The markers are visible on x-ray, CT, MR, or other imaging technique and a device that delivers external beam radiation therapy can use the markers to plan and localize radiation delivery. The detection of fiducial gold markers is useful during automatic on-line megavoltage position verification using a marker extraction kernel (MEK). The markers allow for accurate tumor location three-dimensionally throughout the treatment. Alternatively, it is envisioned that the lumen 460 may be used with a pusher to deliver the markers.

Similarly, the needle 410 can be used to implant seeds for brachytherapy, as one skilled in the art will realize. The added navigation accuracy of the catheter 10 made possible by the combination of the location system 100 and the optic system 200 makes the catheter 10 an ideal vehicle for the precise delivery of brachytherapy seeds.

Positive results have been obtained using a needle 410 that is an NMPE needle with a three-sided Trocar stylet. This particular needle 410 was made with 18-gauge thin-walled tubing and has an echogenically enhanced tip for use in combination with ultrasonically guided implants. The needle 410 also has an outer cannula chamber for smooth transition.

Existing seed implant needles may also be used in combination with the present disclosure. One example of an existing seed implant needle is the Bard BrachyStar® Needle.

Steering System 500

The steering system 500 may utilize any combination of retractable wires and/or pre-formed bends. One embodiment of a steering mechanism 500 is shown on the catheter tip 30 of FIG. 15. Represented is a cross-section of the distal end of a catheter 10. The steering mechanism 500 includes a distal housing 510 that contains the location system 100, defines the distal end of the working channel 20, and seals the end of the catheter 10. The distal housing 510 also defines one or more (in this case four) steering wire lumens 520 for receiving steering wires 530. The steering wire lumens 520 extend the length of the catheter 10 but the portions of the lumens 520 defined by the distal housing 510 are slightly larger to accommodate an anchor ball 540 at the distal ends of the steering wires 530. At a proximal end of the lumen 520, the diameter narrows to that of the steering wire 530, thereby creating a shoulder 550 against which the anchor ball 540 acts when pulled.

Figure 15:
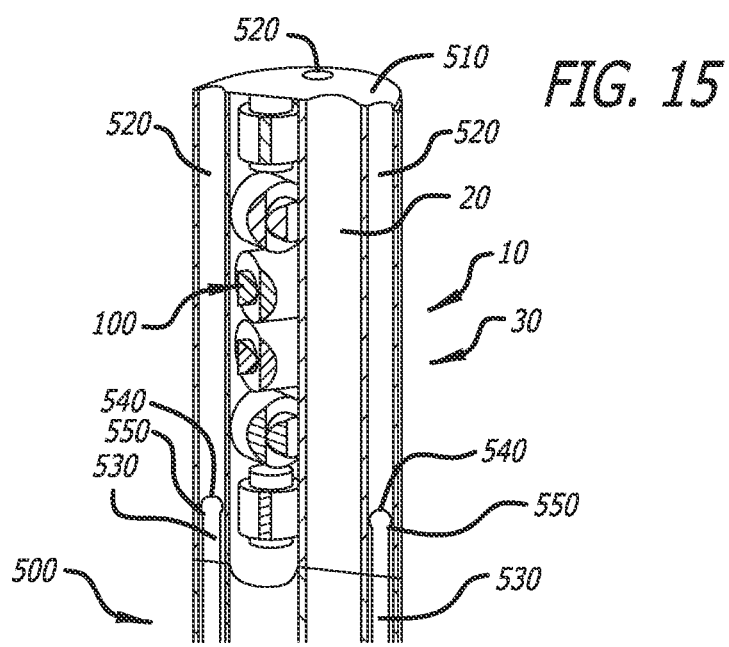
FIG. 15 is a cutaway perspective view of an embodiment of a distal tip of a catheter of the present disclosure.
Figure 16:
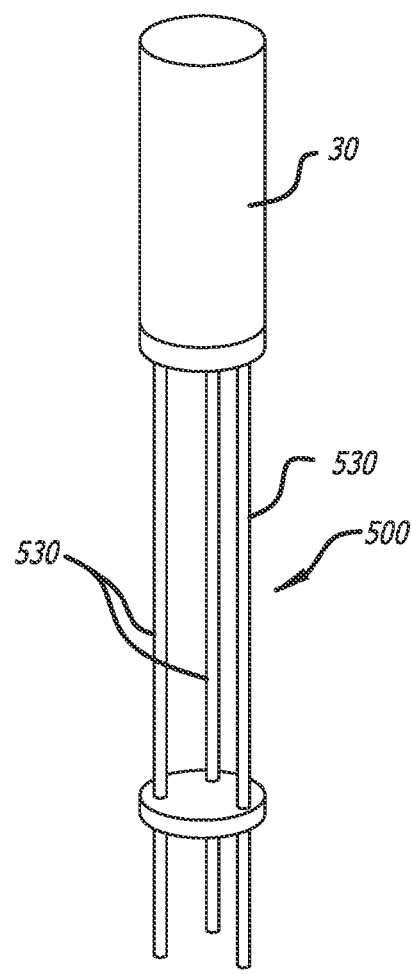
FIG. 16 is a perspective view of an embodiment of a steering system of the present disclosure.
Figure 17:
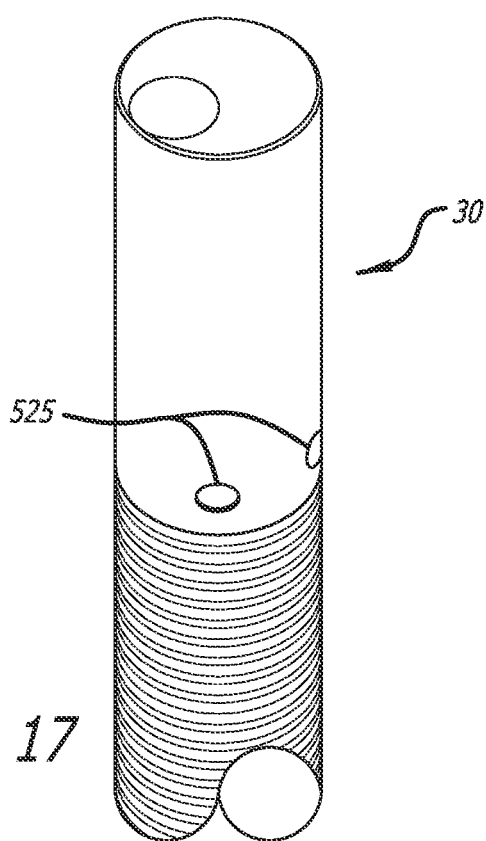
FIG. 17 is a perspective view of an embodiment of a distal tip of a catheter of the present disclosure.

FIGS. 16-19 show a variation on the design of FIG. 15 in which three steering wires 530 are used instead of four. As seen in FIG. 17, the steering mechanism 500 extends from the proximal side of the catheter tip 30 and includes three steering wires 530 spaced 120 degrees apart.

Figure 18:
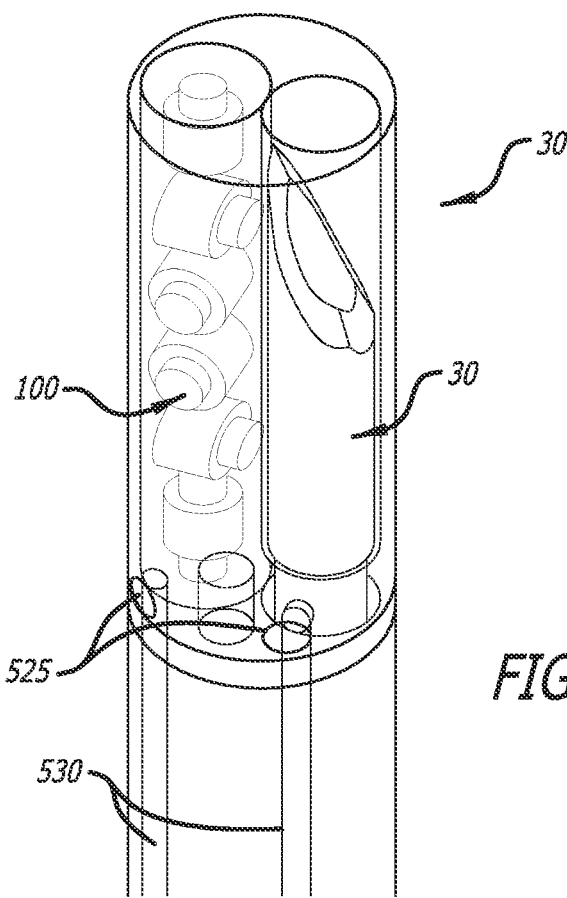
FIG. 18 is a see-through view of an embodiment of a distal tip of a catheter of the present disclosure.
Figure 19:
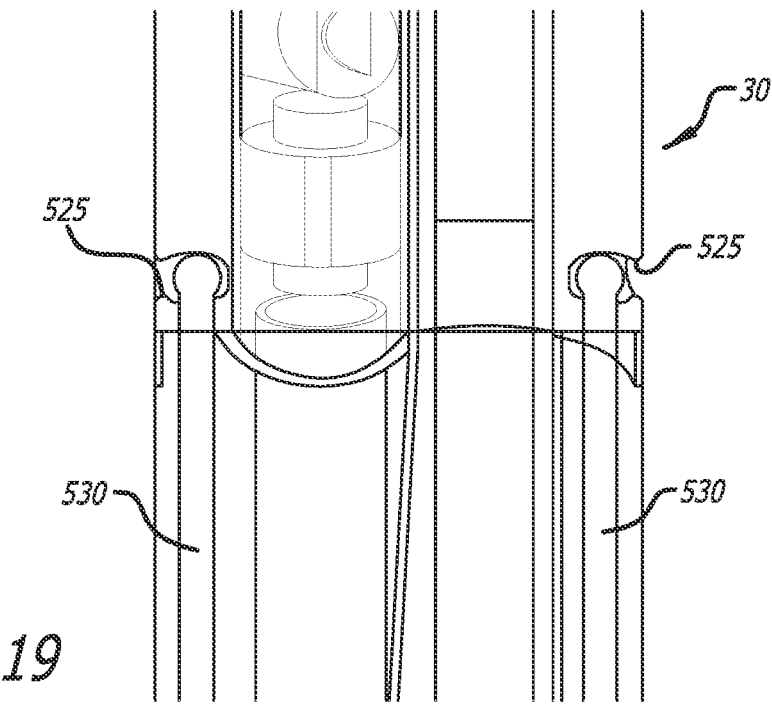
FIG. 19 is a close up of a portion of the distal tip of the catheter shown in FIG. 18.

As shown in FIGS. 17-19, rather than extending the steering wire lumens 520 to the distal end of the catheter tip 30, access ports 525 are provided such that the steering wires 530 may be routed into the sides of the catheter tip 30 and down to the proximal end of the catheter 10.

Figure 20:
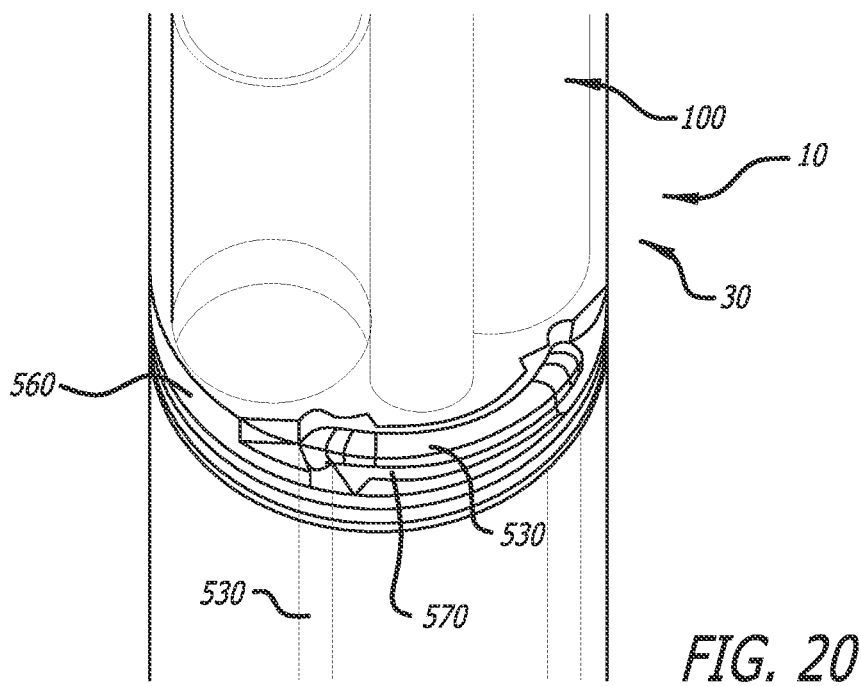
FIG. 20 is a close up of a portion of an embodiment of a distal tip of a catheter of the present disclosure.

FIG. 20 shows another embodiment of a steering system 500 of the present disclosure. Here, a manifold 560 is provided that separates the catheter tip 30 from the rest of the catheter 10. The manifold 560 includes channels 570 that route a steering wire 530 around the periphery of the disk 560 and back toward the proximal end of the catheter. Thus, one steering wire 530 becomes looped and effectively becomes two steering wires.

Examples of other steering mechanisms that may be used with the catheter 10 of the present disclosure include, but are not limited to, those discussed in U.S. Pat. No. 6,702,780 to Gilboa et al.

Catheter Design

The catheter body 600 is flexible and carries all of the lumens, steering wires, tools, etc. that are employed by the various tip 30 designs of the present disclosure. Hence, this section will largely consist of a discussion of the various arrangements envisioned by the present disclosure. Common to all embodiments, is that the body 600 is preferably sized to fit within the working channel of a typical bronchoscope. Notably, however, the minimum bending radius of the body 600, while inside the working channel of the bronchoscope, is advantageously reduced by a reduced tip 30 length, as shown in FIG. 21.

Figure 21:
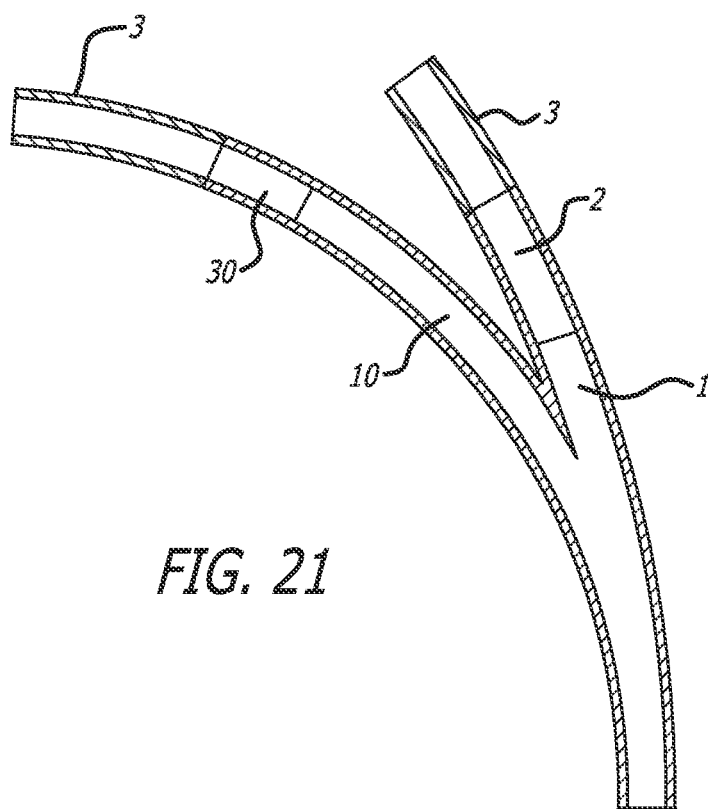
FIG. 21 is a comparison of the bending radius of two catheters having different rigid tip lengths.

More specifically, FIG. 21 shows a comparison between a prior art catheter 1 with a longer tip 2 and a catheter 10 of the present disclosure with a shorter tip 30. Both catheters 1 and 10 have the same diameter and are contained within identical working channels 3. The bending radius is limited by the length of the non-flexible tips 2 and 30. A shorter tip 30 allows a tighter bending radius.

Figure 22:
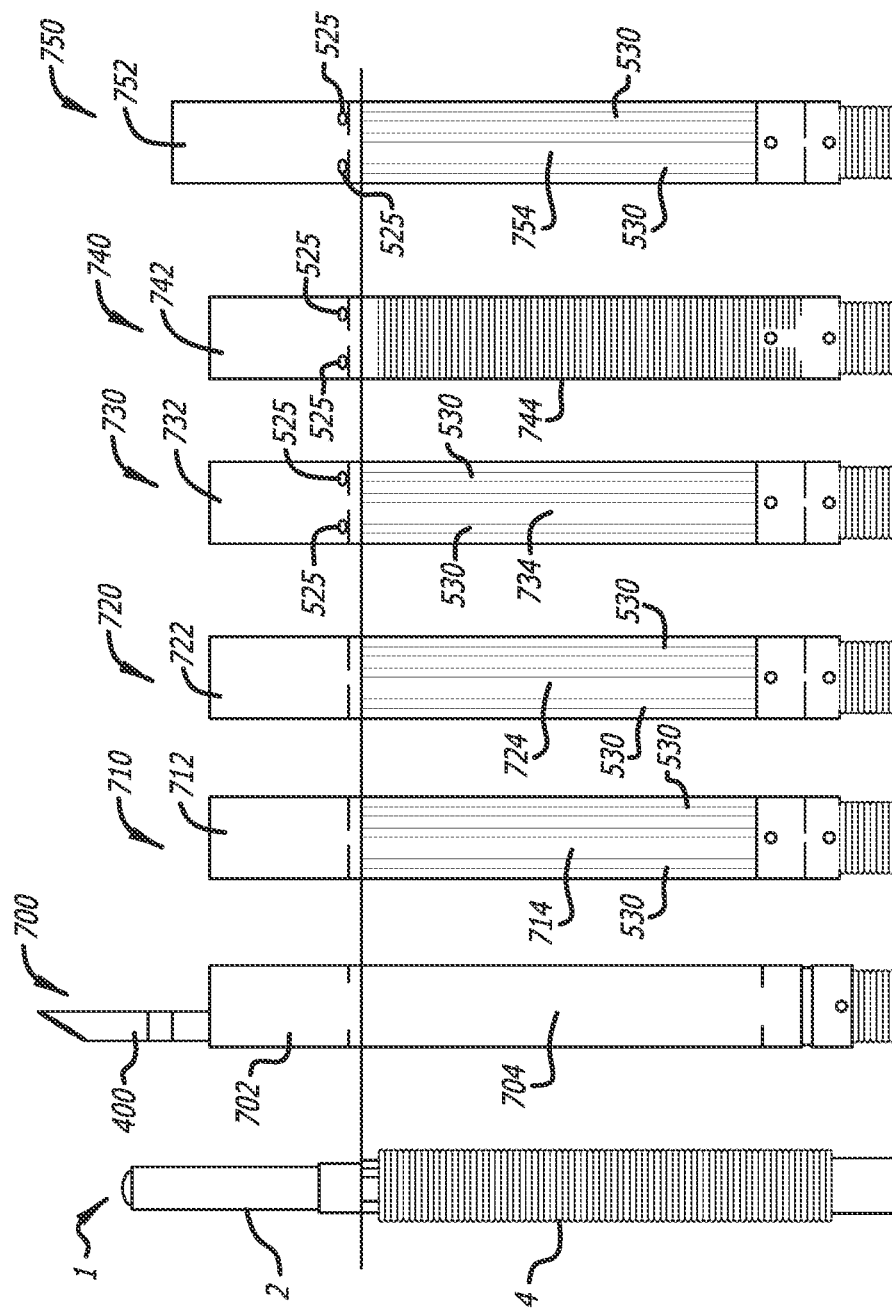
FIG. 22 is an elevation view of several embodiments of distal tips of catheters of the present disclosure juxtaposed to compare sizes.
Figure 23:
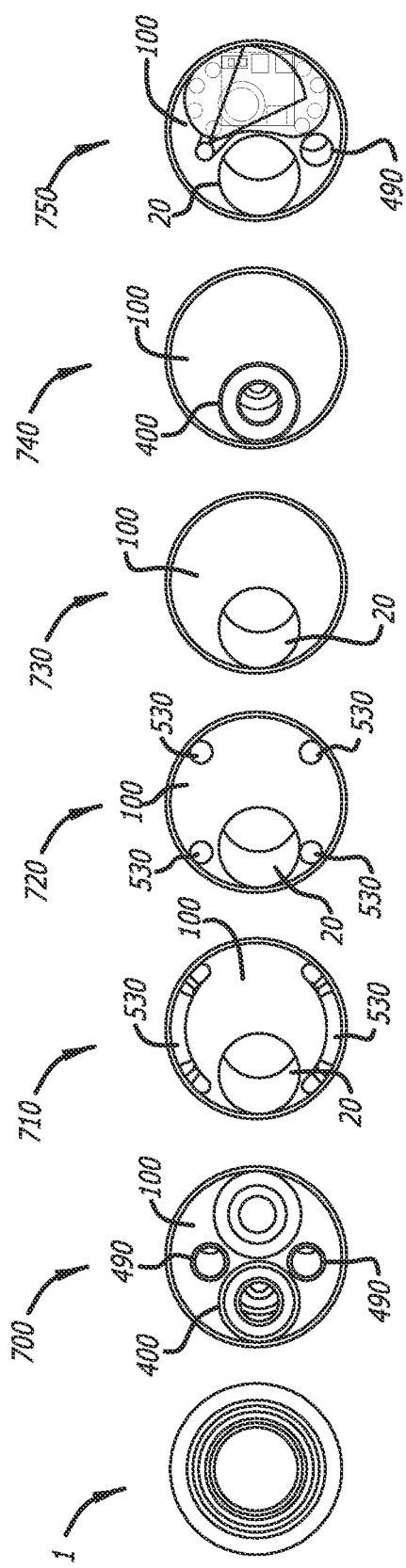
FIG. 23 is an end view of several embodiments of distal tips of catheters of the present disclosure juxtaposed to compare sizes.

Several examples of different configurations of catheters 10 of the present disclosure are shown in FIGS. 22-23. The configurations are juxtaposed adjacent a prior art catheter 1 to show differences in sizes. FIG. 22 shows elevations of the various catheters while FIG. 23 shows corresponding end views of the distal tips.

The prior art catheter 1 has a tip 2 attached to a flexible, steerable segment 4. The tip 2 is 10.2 mm long and has a diameter that is less than 2.65 mm. However, the location sensor 100 occupies substantially all of the tip 2.

Configuration 700 includes a tip 702 attached to a flexible, steerable segment 704. The tip 702 contains a 19 Ga needle 400, a sensor 100 and two irrigation lumens 490, one for irrigation fluid supply and one for applying suction. The tip 702 is 6.8 mm long and the flexible, steerable segment 704 is constructed of a flexible material such as nylon.

Configuration 710 includes a tip 712 attached to a flexible, steerable segment 714. The tip 712 contains a 1.2 mm working channel, a sensor 100, and two looped steering wires 530. The tip 712 is 6.4 mm long and the flexible, steerable segment 714 is constructed of transparent flexible nylon.

Configuration 720 includes a tip 722 attached to a flexible, steerable segment 724. The tip 722 contains a 1.2 mm working channel, a sensor 100, and four steering wires 530.

The tip 722 is 6.4 mm long and the flexible, steerable segment 724 is constructed of transparent flexible nylon.

Configuration 730 includes a tip 732 attached to a flexible, steerable segment 734. The tip 732 contains a 1.2 mm working channel and a sensor 100, and four access ports 525 containing the distal ends of four steering wires 530. The tip 722 is 6.4 mm long and the flexible, steerable segment 724 is constructed of transparent flexible nylon.

Configuration 740 includes a tip 742 attached to a flexible, steerable segment 744. The tip 742 contains a 1.2 mm working channel with a needle 400 contained therein, a sensor 100, and four access ports 525 containing the distal ends of four steering wires 530. The tip 722 is 6.4 mm long and the flexible, steerable segment 724 is constructed of a flexible spring segment.

Configuration 750 includes a tip 752 attached to a flexible, steerable segment 754. The tip 752 contains a 1.2 mm working channel, a sensor 100, four access ports 525 containing the distal ends of four steering wires 530, an irrigation lumen 490, an optic system 200, and an optic cleaning system 300. The tip 752 is 8.5 mm long to accommodate the optic system 200 and the flexible, steerable segment 754 is constructed of a flexible material such as nylon.

Although the disclosure has been described in terms of particular embodiments and applications, one of ordinary skill in the art, in light of this teaching, can generate additional embodiments and modifications without departing from the spirit of or exceeding the scope of the claimed disclosure. Accordingly, it is to be understood that the drawings and descriptions herein are proffered by way of example to facilitate comprehension of the disclosure and should not be construed to limit the scope thereof.

The invention claimed is:

1. A catheter system for performing a lung procedure, comprising:
   a flexible biopsy needle configured to biopsy tissue from a target area in a patient's lung, the flexible biopsy needle having a longitudinal lumen configured to receive the tissue;
   a control system;
   a flexible catheter in communication with the control system and configured to be received within the patient's lung, the catheter having a lumen configured to receive the flexible biopsy needle therethrough;
   a plurality of optical fibers for illuminating airways of the patient's lung;
   a plurality of steering wires disposed within the flexible catheter for steering the flexible catheter within the airways of the patient's lung; and
   a camera in communication with the control system for visualizing the airways of the patient's lung during navigation of the flexible catheter therethrough.

2. The catheter system according to claim 1, wherein the plurality of optical fibers are permanently disposed within the flexible catheter.

3. The catheter system according to claim 1, further comprising a disk disposed within the flexible catheter and configured to receive the plurality of steering wires therethrough.

4. The catheter system according to claim 1, wherein the outer diameter of the lumen is greater than 1 millimeter.

5. The catheter system according to claim 1, wherein the outer diameter of the lumen is less than 2.1 millimeters.

6. The catheter system according to claim 1, wherein each optical fiber of the plurality of optical fibers extends proximally along the flexible catheter from a distal end that terminates at a distal tip of the flexible catheter.

7. The catheter system according to claim 1, wherein at least one optical fiber of the plurality of optical fibers is disposed within a longitudinal channel defined within the flexible catheter.

8. The catheter system according to claim 1, wherein the plurality of steering wires comprises three steering wires.

9. The catheter system according to claim 1, wherein each steering wire of the plurality of steering wires extends proximally along the flexible catheter from a distal end that terminates at a distal tip of the flexible catheter.

10. The catheter system according to claim 1, wherein the gauge of the flexible biopsy needle is greater than 18 G.

11. The catheter system according to claim 1, wherein the flexible biopsy needle has a distal tip portion including a tapered tip configured to pierce tissue, a first flexible portion extending proximally from a proximal end of the distal tip portion, and a second flexible portion extending proximally from a proximal end of the first flexible portion and having an outer diameter greater than an outer diameter of the distal tip portion and an outer diameter of the first flexible portion.

12. The catheter system according to claim 1, wherein the outer diameter of the flexible catheter is greater than 2.5 millimeters.

13. The catheter system according to claim 1, wherein the flexible biopsy needle is configured to deliver a fiducial marker to the patient's lung via the longitudinal lumen of the flexible biopsy needle.

14. The catheter system according to claim 1, wherein the plurality of optical fibers is configured to be coupled to a light source.

15. The catheter system according to claim 1, further comprising a location system in communication with the control system, wherein the location system includes an electromagnetic sensor operatively coupled to the flexible catheter.

16. A catheter system for performing a lung procedure, comprising:
   a flexible biopsy needle configured to biopsy tissue from a target area in a patient's lung, the flexible biopsy needle having:
      a distal tip portion configured to pierce tissue;
      a longitudinal lumen configured to receive the tissue;
      a first flexible portion extending proximally from a proximal end of the distal tip portion; and
      a second flexible portion extending proximally from a proximal end of the first flexible portion;
   a control system;
   a flexible catheter in communication with the control system and configured to be received within the patient's lung, the flexible catheter having a lumen configured to receive the flexible biopsy needle therethrough; and
   an optic system configured to be received within the flexible catheter, the optic system including:
      a plurality of optical fibers configured to be coupled to a light source for illuminating airways of the patient's lung; and
      a camera for visualizing the airways of the patient's lung during navigation of the flexible catheter therethrough.

17. The catheter system according to claim 16, further comprising a plurality of steering wires disposed within the flexible catheter for steering the flexible catheter within the airways of the patient's lung.

18. The catheter system according to claim 16, wherein the outer diameter of the flexible catheter is greater than 2.5 millimeters.

19. The catheter system according to claim 16, wherein the plurality of optical fibers are permanently disposed within the flexible catheter.

20. The catheter system according to claim 16, further comprising a location system in communication with the control system, wherein the location system includes an electromagnetic sensor operatively coupled to the flexible catheter.

21. A catheter system for performing a lung procedure, comprising:
- a flexible biopsy needle configured to biopsy tissue from a target area in a patient's lung;
- a control system;
- a flexible catheter in communication with the control system and configured to be received within the patient's lung, the flexible catheter having a lumen configured to receive the biopsy needle therethrough;
- a plurality of optical fibers for illuminating airways of the patient's lung;
- a camera in communication with the control system for visualizing the airways of the patient's lung during navigation of the flexible catheter therethrough; and
- a plurality of steering wires disposed within the flexible catheter for steering the flexible catheter within the airways of the patient's lung.

22. The catheter system according to claim 21, wherein the flexible biopsy needle includes:
- a distal tip portion having a tapered tip configured to pierce tissue;
- a longitudinal lumen configured to receive the tissue;
- a first flexible portion extending proximally from the distal tip portion; and
- a second flexible portion extending proximally from the first flexible portion and having a diameter larger than the distal tip portion and the first flexible portion.

23. The catheter system according to claim 21, further comprising a location system in communication with the control system, wherein the location system includes an electromagnetic sensor operatively coupled to the flexible catheter.

* * * * *